United States Patent [19]

Peignier et al.

[11] Patent Number: 5,739,153

[45] Date of Patent: Apr. 14, 1998

[54] ARYLPYRAZOLE FUNGICIDES

[75] Inventors: Raymond Peignier, Caluire; Richard Cantegril, Lyons, both of France

[73] Assignee: Rhone-Poulenc Agrochimie, Lyons Cedex, France

[21] Appl. No.: 557,192

[22] PCT Filed: May 31, 1994

[86] PCT No.: PCT/FR94/00628

§ 371 Date: May 31, 1996

§ 102(e) Date: May 31, 1996

[87] PCT Pub. No.: WO94/29276

PCT Pub. Date: Dec. 22, 1994

[30] Foreign Application Priority Data

Jun. 3, 1993 [FR] France ................... 93 06878

[51] Int. Cl.$^6$ ................ A01N 43/56; C07D 231/12
[52] U.S. Cl. .............. 514/406; 544/60; 544/140; 548/364.1; 548/365.7; 548/375.1
[58] Field of Search ............... 548/365.7, 375.1; 514/406

[56] References Cited

U.S. PATENT DOCUMENTS 5,663,119 9/1997 Chene et al. ................... 548/356.1

FOREIGN PATENT DOCUMENTS 0433899 6/1991 European Pat. Off. .
0538156 4/1993 European Pat. Off. .
3620825 12/1987 Germany .

*Primary Examiner*—Robert W. Ramsuer
*Attorney, Agent, or Firm*—Burns, Doane, Swecker & Mathis, L.L.P.

[57] ABSTRACT 3-arylpyrazole derivatives of the formula

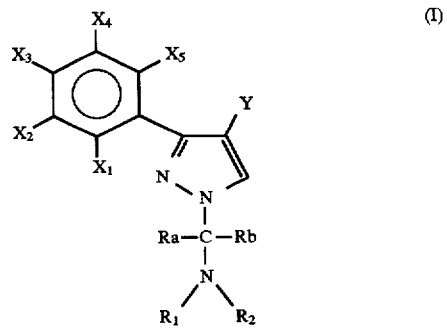

in which $X_1$, $X_2$, $X_3$, $X_4$ and $X_5$, which are the same or different, are H, Hal, nitro, alkyl, alkoxy, Y is H, Hal, nitro, CN, alkyl, alkoxy, alkylthio or an optionally substituted amino; Ra is H, R(alkyl, phenyl, Het), C(V)-V'Ro or C(V)NR$_0$R'$_0$ where: V and V' are O, S; R$_0$ and R'$_0$, H, R, R' optionally substituted by α, which can be GR$_1$, NZ$_1$Z$_2$, SO$_2$NZ$_1$Z$_2$, CVZ$_1$Z$_2$, Rb is H or can form with Ra a hydrocarbon ring of 4–6 C. R$_1$ and R$_2$ are H, R$_0$, R$_3$, G1-T1-Rc, C(O)R$_0$, NTT'. Said fungicides are useful in agriculture.

17 Claims, No Drawings

ARYLPYRAZOLE FUNGICIDES

This application is a 371 of PCT/FR94/00628 filed May 31, 1994.

The subject of the present invention is new derivatives of the family of 3-arylpyrazoles, processes for their preparation, the compositions containing them and their use for protecting plants against fungal diseases.

The subject of the invention more especially is 3-arylpyrazoles, their salts, their N-oxide derivatives and their metallic and metalloid complexes of formulae I and Ia:

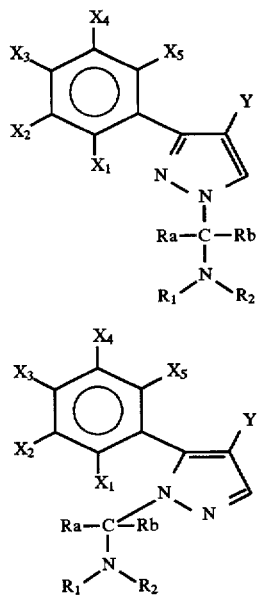

in which:

$X_1$, $X_2$, $X_3$, $X_4$ and $X_5$, which may be identical or different, are:

—a hydrogen or halogen atom, a hydroxyl, mercapto, cyano, thiocyanato, nitro or nitroso group, an amino group optionally substituted with one or two alkyl or phenyl or acyl groups, imines, enamines, amidines and guanidines derived from this amino group;

—an alkyl, hydroxyalkyl, alkoxyalkyl, alkylthioalkyl, alkylsulphinylalkyl, alkylsulphonylalkyl, benzyl, alkenyl, alkynyl, cyanoalkyl, alkoxy, alkenyloxy, formyl, acetyl, alkyl- or alkoxy(thio)carbonyl, mono- or dialkylamino(thio) carbonyl, iminocarbonyl, mono- or diarylamino(thio) carbonyl, carboxyl, carboxylate, carbamoyl or benzoyl radical, —a phenyl, phenoxy or phenylthio radical, —an alkyl- or alkoxy- or mono- or dialkylamino- or phenyl-sulphenyl or -sulphinyl or -sulphonyl radical, —a phosphoryl group substituted with two groups chosen from the group comprising alkyl, alkoxy, alkylthio, dialkylamino, benzyloxy, phenyloxy and phenyl, —a trialkyl- or alkylphenylsilyl group, it being understood that in all the above hydrocarbon definitions, the alkyl part of these groups may contain from 1 to 4 carbon atoms and be optionally halogenated and that phenyl denotes the optionally substituted phenyl ring.

Two of the adjacent $X_1$, $X_2$, $X_3$, $X_4$ and $X_5$ groups may also form a carbon ring containing 5 to 7 members in total, which may include one or more following atoms or groups: O, S, N, C=O, C=S, SO, $SO_2$, CH=CH. The carbons of this bridge may be unsubstituted or substituted with at least one halogen atom and/or at least one hydroxyl, alkoxy, alkylthio, mono- or dialkylamino, alkylsulphinyl or -sulphonyl group, the alkyl part being as defined above, with the proviso that at least one of the X groups is other than hydrogen;

Y is:

—a hydrogen or halogen atom,

—a hydroxyl or mercapto group and their formylated or alkyl- or alkoxy- or amino(thio)acylated derivatives, it being possible for the amino group to be optionally substituted, —a nitro, cyano, thiocyanato or azido group, —an alkyl, alkenyl, alkynyl, alkoxy or alkylthio group, each of these groups being optionally halogenated, —an acyl or thioacyl radical which may be: a formyl radical, an alkyl- or alkenyl-carbonyl or -thiocarbonyl group, it being possible for the alkyl or alkenyl radical to be linear or branched, —an alkoxy- or alkylthio- or amino- or monoalkylamino- or dialkylamino- or phenylamino- or alkylphenylamino-(thio)-carbonyl group, —a carboxyl group or and its salts, —an optionally substituted phenoxy, —an amino unsubstituted or substituted with one or two alkyls or phenyls, —an alkylsulphinyl or alkylsulphonyl group, the alkyl part being as defined above, $Y_1$ and $X_5$ or $Y_2$ and $X_1$ may also form a carbon ring containing 5 to 7 members in total, which may include one or more following atoms or groups: O, S, N, C=O, C=S, SO, $SO_2$, CH=CH. The carbons of this bridge may be unsubstituted or substituted with at least one halogen atom and/or at least one hydroxyl, alkoxy, alkylthio, mono- or dialkylamino, alkylsulphinyl or -sulphonyl group, the alkyl part being as defined above;

Ra is

—a hydrogen atom,

—a radical R which may be:
 —1 to 6 C alkyl (optionally substituted with GR7)
 —(3 to 7 C)cycloalkyl, (3 to 7 C)cycloalkyl (1 to 4 C) alkyl optionally substituted with GR3 (defined below))
 —phenyl, a heterocycle Het (defined below), phenyl(1 to 4 C)alkyl, Het(1 to 4 C)alkyl, optionally substituted with 1 to 8 halogen atoms and GR4 (defined below)).

—a group $C(V)$-$V'R_0$ or $C(V)NR_0R'_0$, in which:
 —V and V', which may be identical or different, are an oxygen or sulphur atom, and
 —$R_0$ and $R'_0$, which may be identical or different, may be is a hydrogen atom, the radicals R or R', optionally substituted with a group α which may be a group $GR_1$ (defined below), $NZ_1Z_2$, $SO_2NZ_1Z_2$, $CVZ_1Z_2$, in which V is as defined above and $Z_1$ and $Z_2$ are a hydrogen atom or the radical R, which may in addition optionally substituted with GR2 (defined below).

Rb is a hydrogen atom or may form with Ra a 4 to 6 C hydrocarbon ring.

$R_1$ is:

—1) $R_0$, in which $Z_1$ and $Z_2$ may in addition form, with the nitrogen atom to which they are attached, a radical Het (defined below), optionally substituted with GR3 (defined below); or a radical R' which may be: alkenyl, alkynyl, phenylalkenyl, phenylalkynyl, Hetalkenyl or Hetalkynyl, the alkenyl or alkynyl part of these radicals having from 2 to 6 C.

3

When R1 is a group R0, and more precisely when R0 is Het(1 to 4 C)alkyl, it may more specifically be a group of formula IIa or IIb,

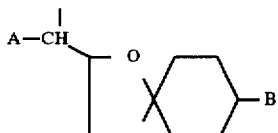

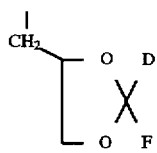

in which,

V has the same meaning as above,

A is a hydrogen atom or a methyl group, with the proviso that V is an oxygen atom when A is a methyl group.

B is a group: (1 to 14 C) alkyl, (3 to 7 C)cycloalkyl, cycloalkylalkyl (3 to 7 C; I to 8 C for the alkyl part), (6 to 10 C)aryl, aralkyl (6 to 10 C; 1 to 8 C for the alkyl part).

D is a group:

(1 to 14 C) alkyl, haloalkyl (1 to 14 C for the alkyl part; 1 to 6 halogen atoms), cyanalkyl (1 to 4 C for the alkyl part), aralkyl, aryloxy(thio)alkyl, arylsulphi(o)nylalkyl, aralkyloxy(thio)alkyl (6 to 10 C for the aryl part; 1 to 8 C for the alkyl part; the aryl part optionally substituted with one several substituent(s) chosen from the group GR4).

F, which may be identical to or different from D, and which may have the same meanings, may additionally be a hydrogen atom.

—2) $R_3$, which may be:

—a hydrogen atom,

—a group $SO_2W_1$, in which $W_1$ is the group R or R',

—a group $C(V)W_2$, in which $W_2$ is a group $R_0$, $VR_0$ or $NR_0R'_0$, in which $R_0$ is defined as above, —a group $P(V)W3$, W'3 in which W3, W'3, which may be identical or different, may be a group R, VR or R', it being possible in addition for W3, W'3 to form, with the phosphorus atom to which they are attached, a radical Het, optionally substituted with GR4 (defined below), —a group $CW_4=N-W'_4$, in which $W_4$ and $W'_4$, which may be identical or different, may be a nitro, cyano, $R_0$, $VR_0$, $C(V)V'R_0$ or $C(V)NR_0R'_0$ group, in which $R_0$ and $R'_0$ are as defined above, it being possible in addition for $R_0$, for $C(V)V'R_0$, to be an alkali metal or alkaline-earth metal atom; it being possible in addition for $W_4$ and $W'_4$ to form, with the nitrogen atom to which they are attached, a radical Het, optionally substituted with GR3 (defined below, —3) a group G1-T1-Rc, in which:

—G1 is a group SO2, C(V), P(V)W3 or C=N-W4,

—T1 is V, CH or Cα, it being possible in addition for G1 and T1 to form a group N=CW4, the symbols V, W3, W4 and α being as defined above;

—Rc is a 1 to 6 C alkyl;

—4) a group $C(O)-R_0$, in which $R_0$ is as defined above,

—5) a group NTT', in which:

—T is $R_0$, G1-T1-Rc or N=CW3W4 and T' is $R_0$ or $R_3$, Rc, G2-T2 Rc or G1-T1 Rc;

4

$R_0$, $R_3$, Rc, G1, G2, T1 and T2 being as defined above;

G2 and T2 being respectively identical to or different from G1 and T1; and it not being possible for T and T' together to be a hydrogen atom and it being possible for them to form a morpholino or piperidino group;

—6) a group $C(CRaRbNR_4)_nCRaRbR_4$, in which n is equal to zero or 1, Ra and Rb are defined as above, $R_4$ is a radical of formula:

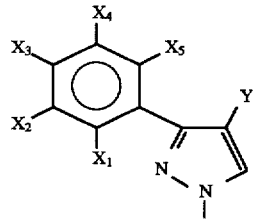

and $R_5$ is $R_1$ or $CRaRbR_2$.

—7) a group C(L)NT'T", in which L is V, T" is $R_0$, G1-T1-Rc or $CRaRbR_4$, and in which Ra, Rb, $R_4$, V and T' are as defined above, it not being possible for T' and T" simultaneously to represent a hydrogen atom and it being possible for them to form a morpholino or piperidino group;

$R_2$, which may be identical to or different from $R_1$, and which may have the same meanings, that is to say which may be $R_0$, $OR_0$, $R_3$, Rc, G1-T1-Rc, G2-T2-Rc and $CRaRbR_4$, with the proviso that they are not simultaneously a hydrogen atom, it being possible in addition for $R_1$ and $R_2$ to form, with the nitrogen atom to which they are attached:

—a nitrogen-containing radical Het, optionally substituted With GR3, preferably a morpholino or piperidino; or pyrazolidino;

—a group N=CH-W5, in which W5 is R, Rb being a hydrogen atom, and the substituted ammonium salts (halides, carboxylates and sulphates) and substituted imidinium salts of these compounds, When R1 is a group of formula IIa or IIb, R2 is then a hydrogen atom or a group R defined as above, given that, in the preceding text, except where especially mentioned:

"alkyl" denotes an alkyl containing from 1 to 4 carbon atoms,

"cycloalkyl" denotes a cycloalkyl containing from 1 to 4 carbon atoms,

"alkenyl" or "alkynyl" denotes an alkenyl or alkynyl having from 2 to 5 carbon atoms, "Het" is a mono- or bicyclic heterocyclic radical containing from 5 to 10 carbon atoms, of which 1 to 4 are N, O, S or P.

GR1 is:

—a halogen atom or a nitro or cyano group,

—a group R, R', OR, RS(O)m, with m equal to 1 to 3, RC(V)V' or R'C(V)V'.

GR2 is:

—a halogen atom or a nitro or cyano group,

—a group R, R', OR, RS(O)m, with m equal to 1 or 3, RC(V)V' or R'C(V)V'.

—a mono- or dialkylamino, mono- or dialkylamino(thio) carbonyl, mono- or dialkylaminosulphonyl group, GR3 is:

—a halogen atom or a nitro or cyano group,
—a group R, OR, RS(O)m, with m equal to 1 or 3, RC(V)V' or
—a mono- or dialkylamino, mono- or dialkylamino(thio) carbonyl, mono- or dialkylaminosulphonyl group,
GR4 is:
—a halogen atom or a nitro or cyano group,
—alkyl, alkoxy, alkylsulphenyl, alkylsulphonyl, alkyl (thio)carbonyl, alkoxy(thio)carbonyl,
—a mono- or dialkylamino, mono- or dialkylamino(thio) carbonyl, mono- or dialkylaminosulphonyl group,
GR5 is:
—a halogen atom or a nitro or cyano group,
—a group R, R', OR, RS(O)3, RC(V)V' or R'C(V)V',
—a mono- or dialkylamino, mono- or dialkylamino(thio) carbonyl, mono- or dialkylaminosulphonyl group,
GR6 is GR5 except for R' and R'C(V)V',
GR7 is GR2 except for alkyl;
all the radicals of these substituents being defined above.

Preferred compounds are those in the formula for which X1 to X5 are chosen from the group comprising a hydrogen or halogen atom, cyano, nitro or an alkyl radical having from 1 to 4 carbon atoms or two neighbouring X groups form, with the phenyl, an optionally halogenated benzodioxole.

Other preferred compounds are those in the formula for which Y is a halogen atom or a cyano group.

Other preferred compounds are those in the formula for which Ra and Rb, which may be identical or different, are a hydrogen atom or an alkyl having from 1 to 4 carbon atoms.

Other preferred compounds are those in the formula for which $R_1$ and $R_2$, which may be identical or different, are a radical R.

Other preferred compounds are those in the formula for which $R_1$ and $R_2$, which may be identical or different, are an alkyl having from 1 to 4 carbon atoms.

Other preferred compounds are those in the formula for which $R_1$ and $R_2$ form, together with the nitrogen atom which bears them, a morpholino, piperidino, pyrrolidino, imidazolyl, triazolyl, pyrazolyl or benzoxazinyl group.

The compounds of formula I according to the invention may be prepared according to various processes.

According to a first process for the preparation of compounds of formula I, in which $R_1$ and $R_2$, which may be identical or different, are chosen from $R_0$, an aldehyde RaCH(O) or of a ketone RaRbC(O) is reacted, in the presence of an amine $R_1R_2NH$, with a phenyl- pyrazole of formula II-H:

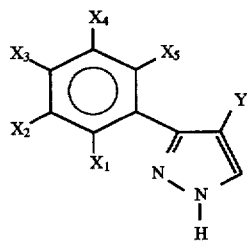

III in which $X_1$, $X_2$, $X_3$, $X_4$ and $X_5$ and Y have the same meanings as in the formula I, at a temperature between room temperature and the reflux point, in a solvent medium, optionally in the presence of a catalytic amount of strong acid.

As example of a solvent medium it is generally possible to use an aromatic solvent or mixture of solvents chosen from the group comprising toluene and xylene, or an aprotic solvent or mixture of solvents chosen from the group comprising diethyl ether, tetrahydrofuran, acetone or acetonitrile, or alternatively a polar protic solvent or mixture of solvents chosen from the group comprising water, methanol, ethanol, isopropanol and acetic acid.

As example of a strong acid it is possible to use acetic acid and para-toluenesulphonic acid.

According to a second process for the preparation of substituted ammonium salts or substituted imidinium salts of the compounds of formula I, in which a pyrazole of formula R4CRaRbU, in which R4, Ra and Rb are defined as above and U is a halogen atom or a group which may be released such as mesyl or tosyl, is reacted with a stoichiometric amount of an aliphatic or heterocyclic tertiary amine $RNR_1R_2$ containing at least one nitrogen which may be salified, at a temperature between room temperature and the reflux point, in a solvent medium or mixture of solvents, or an aprotic solvent or mixture of solvents chosen from the group comprising acetone and acetonitrile, or alternatively in a polar protic solvent or mixture of solvents chosen from the group comprising methanol and ethanol, or alternatively polar solvents such as N,N-dimethylformamide and N-methylpyrrolidone.

According to a third process for the preparation of compounds of formula I, in which $R_1$ and $R_2$ are a group CRaRbR4, that is to say of formula R4CRaRbNCRaRbR4, characterized in that a hydroxymethyl-pyrazole of formula R4CRaRbOH is reacted with a dimeric pyrazole of formula R4CRaRbNHCRaRbR4 or with formamide, in an aromatic or polar protic solvent medium, at a temperature between room temperature and the reflux point, in a solvent medium, optionally in the presence of a catalytic amount of strong acid.

According to a fourth process for the preparation of compounds of formula I, in which R1 and R2 form, together with the nitrogen atom which bears them, a group N=CH-W5, an aldehyde RaCH(O) is reacted, in the presence of alcoholic ammonia solution, with a phenylpyrazole of formula II defined above, at a temperature between room temperature and the reflux point, in a polar protic solvent medium, optionally in the presence of a catalytic amount of strong acid.

According to a fifth process for the preparation of the compounds of formula I, a pyrazole of formula R4CRaRbU, in which R4, Ra, Rb and U are defined as above, is reacted with 1.0 to 1.5 equivalents of an amine of formula R1R2NH,
—in the presence of 1.0 to 1.5 equivalents of a base chosen from K2CO3, Na2CO3, NaHCO3, Et3N, N,N-dimethylaniline, pyridine, 4-dimethylaminopyridine (DMAP), diazabicyclooctane (DABCO), diazabicyclononene (DBN), diazabicycloundecene (DBU),
—in the presence or absence of a solvent such as toluene, xylenes, chlorobenzenes, cyclohexane, N,N-dimethylformamide (DMF), N,N-dimethylacetamide (DMA), N-methylpyrrolidone (NMP), dimethyl sulphoxide (DMSO), EtOH, i-PrOH and n-BuOH,
—at a temperature between 20° C. and 180° C.

The amines of formula IVa or IVb may be prepared according to the methods, or an adaptation of the methods, described in EP 281,842 and/or DE 3,828,545 and/or DE 3,305,769.

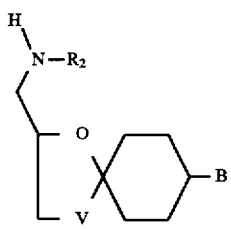

IVa

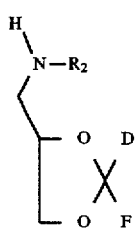

IVb by reacting a heterocycle of formula Va or Vb,

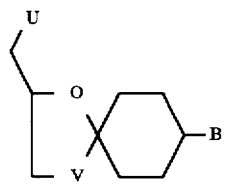

Va

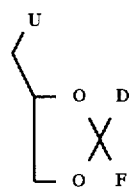

Vb in which,

U, V, B, D and F have the same meaning as above, with 1.0 to 2.5 equivalent(s) of an amine of formula R2NH2, —in the presence of 1.0 to 2.5 equivalent(s) of a base chosen from K2CO3, Na₂CO₃, NaHCO₃, Et₃N, N,N-dimethylaniline, pyridine, 4-dimethylaminopyridine (DMAP), diazabicyclooctane (DABCO), diazabicyclononene. (DBN), diazabicycloundecene (DBU), —in the presence or absence of a solvent such as toluene, xylenes, chlorobenzenes, cyclohexane, N,N-dimethylformamide (DMF), N,N-dimethylacetamide (DMA), N-methylpyrrolidone (NMP), dimethyl sulphoxide (DMSO), EtOH, i-PrOH and n-BuOH, —at a temperature between 20° C. and 180° C.

The heterocycles of formula Va may be obtained by analogy with:

J. Org. Chem., 1973, 38, 834–35.
Tet. Letters 1982, 23, 47–50.
Liebigs Ann. Chem., 1984, 1298–1301.
J. Org. Chem., 1988, 51, 1894–97.
Z. Naturforsch. B. Anorg. Chem., Org. Chem., 1985, 4013, 393–97.

by reacting a cyclohexanone of formula VIa, with 1.0 to 2.0 equivalent(s) of an alcohol of formula VIIa,

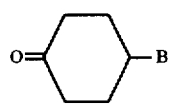

VIa

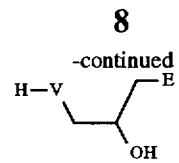

VIIa in which,

V has the same meaning as above,

E is a halogen atom or a hydroxyl group, in a solvent such as toluene, xylenes, chlorobenzenes, cyclohexane, in the presence of a catalytic amount of p-toluenesulphonic acid (PTSA), at a temperature between 40° C. and 150° C.

The heterocycles of the formula Vb may be prepared by analog with:

Rec. Trav. Chim. Pays-Bas 1972, 91, 989–1001; Farm. Ed. Sci. 1974, 29, 167–74;

J. Med. Chem., 1963, 6 (3), 325–28; by reacting a ketone or aldehyde of formula rib, with 1.0 to 2.0 equivalent(s) of an alcohol of the formula VIIb,

VIb

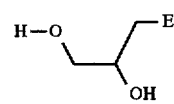

VIIb in which,

D, F and E have the same meaning as above, in a solvent such as toluene, xylenes, chlorobenzenes or cyclohexane, in the presence of a catalytic amount of p-toluene sulphonic acid (PTSA), at a temperature between 40° C. and 150° C.

The cyclohexanones of formula VIa may be prepared by analogy with:

Tet. Letters 1987, 28, 2347–50; Tet. Letters 1986, 27, 2875–78; Tet. Letters 1979, 19, 3209–12; J. Amer. Chem. Soc., 1987, 109, 6887–89; J. Amer. Chem. Soc., 1973, 95, 3646–51; J. Amer. Chem. Soc., 1972, 94, 7599–7600; Bull. Chem. Soc. Jap. 1987, 60, 1721–26, Synth. Commun., 1985, 15, 759–64; Synth. Commun., 1982, 12, 267–77; J. Org. Chem., 1973, 38, 1775–76; U.S. Pat. No. 4,251,398; U.S. Pat. No. 3,960,961; EP 0,002,136; DE 2,636,684; DE 2,509,183; FR 2,231,650.

The amines of formula VIII may be prepared according to the methods, or an adaptation of the methods, described in EP 355,597, by reacting a heterocycle of formula IX,

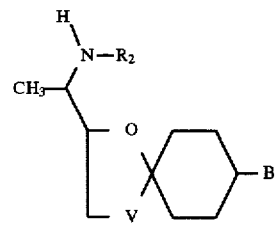

VIII

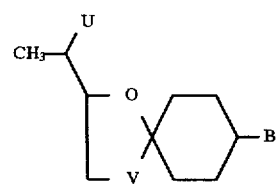

IX in which U and B have the same meaning as above, with 1.0 to 2.5 equivalent(s) of an amine of formula R₂NH₂, under the same conditions described above for the preparation of Va and Vb.

The heterocycles of formula IX may be obtained by reacting a cyclohexanone of formula VIa with 1.0 to 2.0 equivalent(s) of an alcohol of formula X or an oxirane of formula XI.

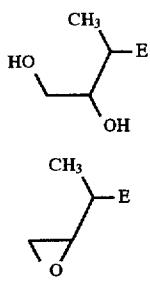

in which E has the same meaning as above, in a solvent such as toluene, xylenes, chlorobenzenes or cyclohexane, in the presence of a catalytic amount of p-toluenesulphonic acid (PTSA), at a temperature between 40° C. and 150° C.

The alcohols of formula X may be prepared by analogy with the processes described in: EP 200,267; DE 2,937,840; U.S. Pat. No. 4,035,178; Tetrahedron 1971, 27, 3197–3205; Tetrahedron 1979, 35, 2583–89.

The oxiranes of formula XI may be prepared according to the processes described in:
J. Amer. Chem. Soc., 1974, 96, 5254–55; Tet. Letters 1977, 17, 4397–400; Tet. Letters 1979, 19, 4733–36; Tet. Letters 1980, 20, 4843–46.

Another subject of the invention is the compounds of formulae R4CRaRbNHCRaRbR4, R4CRaRbOH, R4CRaNHCHO and R4CRaCN, which may be used as intermediates for the preparation of the compounds of formula I according to one of the processes described above.

Another subject of the invention is compositions for the protection of plants against fungal diseases, characterized in that they contain at least one compound of formula I as active material.

The examples which follow are given by way of indication in order to illustrate the preparation and the fungicidal activity of the derivatives according to the invention. The structure of these derivatives was confirmed by NMR analysis.

EXAMPLE 1

1-((2,6-Dimethylmorpholin-4-yl)methyl)-4-chloro-3-(2-nitro-3-chloro)phenylpyrazole One drop of acetic acid is added to a solution of 1.80 g (0.007 mol) of 4-chloro-3-(2-nitro-3-chloro)phenylpyrazole and 0.55 g (0.00735 mol) of aqueous formaldehyde (37%) in 30 ml of ethanol. A solution of 0.85 g (0.00735 mol) of 2,6-dimethylmorpholine in 10 ml of ethanol is added dropwise at room temperature. The mixture is stirred for 5 hours at the same temperature and then concentrated to dryness under reduced pressure. The residual solid is taken up in 50 ml of water and extracted with 50 ml of ethyl ether. The organic phase is dried over $MgSO_4$ and concentrated under reduced pressure. 2.5 g (0.0065 mol) of 1-((2,6-dimethylmorpholin-4-yl)methyl-4-chloro-3- (2-nitro-3-chloro)phenylpyrazole are obtained, melting at 169° C.

The compounds of formula III are prepared as in Example 1:

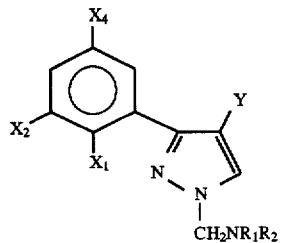

which compounds are summarized in the following table:

| Compound No. | $X_1$ | $X_2$ | $X_4$ | Y | NR1R2 | m.p. (°C.) |
|---|---|---|---|---|---|---|
| 2 | NO2 | Cl | H | Cl | [N-(2-furfuryl)-N-methyl]amino | NMR |
| 3 | NO2 | Cl | H | Cl | 1-pyrrolidinyl | 81 |
| 4 | NO2 | Cl | H | Cl | 3-methyl-1-piperidyl | 139 |
| 5 | NO2 | Cl | H | Cl | 3,5-dimethyl-1-piperidyl | 125 |
| 6 | NO2 | Cl | H | Cl | (N-benzyl-N-methyl)amino | 73 |
| 7 | NO2 | Cl | H | Cl | 1-piperidyl | 120 |
| 8 | NO2 | Cl | H | Cl | N,N-di(cyanoethyl)amino | 143 |
| 9 | NO2 | Cl | H | Cl | Me, (N-cyanoethyl-N-methyl)amine | 110 |
| 10 | NO2 | Cl | H | Cl | 4-morpholinyl | 118 |
| 11 | NO2 | Cl | H | Cl | 4-thiomorpholinyl | 117 |
| 12 | O | CF2O | H | CN | [N-(2-furfuryl)-N-methyl]amino | 80 |
| 13 | O | CF2O | H | CN | 2,6-dimethyl-4-morpholinyl | 129 |
| 14 | NO2 | Cl | H | Cl | diethylamino | 95 |
| 15 | NO2 | Cl | H | Cl | 4-phenyl-1-piperidyl | 149 |
| 16 | NO2 | Cl | H | Cl | N,N-di(methoxyethyl)amino | 83 |
| 17 | NO2 | Cl | H | Cl | 4-methyl-1-piperidyl | 80 |
| 18 | H | Cl | Cl | Cl | [N-cyanoethyl-N-(2-furfuryl]amino | 68 |
| 19 | H | Cl | Cl | Cl | [N-(2-furfuryl)-N-methyl]amino | 62 |
| 20 | H | Cl | Cl | Cl | 2,6-dimethyl-4-morpholinyl | NMR |
| 21 | NO2 | Cl | H | Cl | 4-methyl-1-piperidyl | 92 |

-continued

| Compound No. | X₁ | X₂ | X₄ | Y | NR1R2 | m.p. (°C.) |
|---|---|---|---|---|---|---|
| 22 | NO2 | Cl | H | Cl | 4-benzyl-1-piperidyl | 94 |
| 33 | NO2 | Cl | F | Cl | 2,6-dimethyl-4-morpholinyl | 117 |
| 34 | NO2 | Cl | F | Cl | [N-(2-furfuryl)N-methyl]amino | 101 |
| 35 | F | Cl | H | Cl | 2,6-dimethyl-4-morpholinyl | |
| 36 | F | Cl | H | Cl | [N-(2-furfuryl)-N-methylamino | |

EXAMPLE 2

1-(1-Imidazolyl)methyl-4-chloro-3-(3,5-dichloro)phenylpyrazole (Compound 23)

0.15 ml of 1,8-diazabicyclo[5.4.0]undecen-7-ene is added at room temperature to a solution of 2.55 g (0.01 mol) of 4-chloro-3-(3,5-dichloro)phenylpyrazole and 0.90 g (0.03 mol) of paraformaldehyde in 70 ml of THF. The reaction mixture is stirred for 4 hours at room temperature. A solution of 4.75 g (0.015 mol) of thionyl chloride in 20 ml of THF is run in dropwise at 0° C. and the stirring is continued for 4 hours at room temperature. The reaction mixture is concentrated to dryness. The residue is taken up in 15 ml of heptane and then dried. 2.15 g (0.0073 mol) of 1-chloromethyl-4-chloro-3-(3,5-dichlorophenyl)pyrazole are obtained, melting at 88° C.

1.1 g (0.0074 mol) of sodium iodide are added to a solution of 2.15 g (0.0073 mol) of 1-chloromethyl-4-chloro-3-(3,5-dichloro)phenylpyrazole in 40 ml of anhydrous acetone. The mixture is stirred for 4 hours at room temperature. The sodium chloride is removed by filtration and the reaction medium is diluted with 30 ml of anhydrous DMF. After addition of 0.51 g (0.0075 mol) of imidazole and 1.05 g (0.0076 mol) of K₂CO3, stirring is continued for 2 hours at 60° C. The reaction medium is poured into 250 ml of ice-water. The precipitate is recovered by filtration, washed with 20 ml of water and 20 ml of heptane and dried under reduced pressure. 1.95 g (0.006 mol) of 1-(1-imidazolyl)methyl-4-chloro-3-(3,5-dichloro)phenylpyrazole are obtained, melting at 157° C.

The compounds of formula III, summarized in the following table, are prepared as in Example 2:

| Compound No. | X₁ | X₂ | X₄ | Y | NR1R2 | m.p. (°C.) |
|---|---|---|---|---|---|---|
| 24 | H | Cl | Cl | Cl | 1,2,4-triazol-1-yl | 177 |
| 25 | H | Cl | Cl | Cl | 1-pyrazolyl | 205 |

EXAMPLE 3

1-(1,4-Dihydro-2H-3,1-benzoxazin-1-yl)methyl-4-chloro-3-(3,5-dichloro)phenylpyrazole (Compound 26)

One drop of acetic acid is added to a solution of 2.55 g (0.01 mol) of 4-chloro-3-(3,5-dichloro)phenylpyrazole and 2 ml (0.025 mol) of aqueous formaldehyde (37%) in 30 ml of ethanol. A solution of 1.25 g (0.01 mol) of o-aminobenzyl alcohol in 10 ml of ethanol is run in dropwise and at room temperature. The mixture is stirred for 5 hours at the same temperature and then concentrated to dryness under reduced pressure. The residual solid is taken up in 50 ml of water and extracted with 50 ml of ethyl ether. The organic phase is dried over MgSO₄ and concentrated under reduced pressure. 3.60 g (0.0091 mol) of 1-(1,4-dihydro-2H-3,1-benzoxazin-1-yl)methyl-4-chloro-3-(3,5-dichloro)phenylpyrazole are obtained, melting at 143° C.

EXAMPLE 4

(4-Chloro-3-(3,5-dichloro)phenylpyrazol-1-yl)-triethylammoniummethane chloride (Compound 27)

1.1 g (0.0074 mol) of sodium iodide are added to a solution of 2.15 g (0.0073 mol) of 1-chloromethyl-4-chloro-3-(3,5-dichloro)phenylpyrazole (prepared as in Example 2) in 40 ml of anhydrous acetone. The mixture is stirred for 4 hours at room temperature. The sodium chloride is removed by filtration. 0.76 g (0.0075 mol) of triethylamine is added to the filtrate and the reaction medium is stirred for 12 hours at room temperature. The precipitate is recovered by filtration, washed with 20 ml of heptane and dried under reduced pressure. 2.55 g (0.00525 mol) of (4-chloro-3-(3,5-dichloro)phenylpyrazol-1-yl)methyl-triethylammonium chloride are obtained, melting at 175° C.

EXAMPLE 5

1,1-Bis((4-chloro-3-(3,5-dichloro)phenylpyrazol-1-yl)methyl)-4-(dimethylamino)aniline (Compound 28)

A few crystals of p-toluenesulphonic acid are added to a solution of 2.55 g (0.01 mol) of 4-chloro-3-(3,5-dichloro)phenylpyrazole and 2.4 ml (0.03 mol) of aqueous formaldehyde (37%) in 30 ml of toluene. A solution of 0.70 g (0.005 mol) of 4-(dimethylamino)aniline in 10 ml of toluene is run in dropwise and at room temperature. The mixture is stirred for 5 hours at the reflux temperature and then concentrated to dryness under reduced pressure. The residual solid is taken up in 50 ml of water and 50 ml of heptane, and then dried under reduced pressure. 2.80 g (0.0043 mol) of 1,1-bis((4-chloro-3-(3,5-dichloro)phenylpyrazol-1-yl)methyl)-4-(dimethylamino)aniline are obtained, melting at 181° C.

The compounds of formula IV are prepared as in Example 5

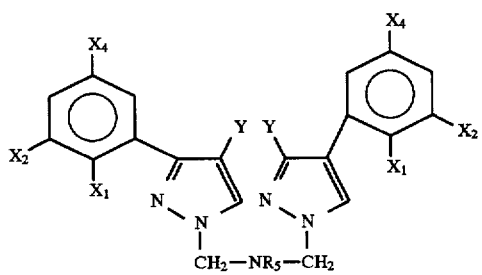

which compounds are summarized in the following table:

| Compound No. | X₁ | X₂ | X₄ | Y | R5 | m.p. (°C.) |
|---|---|---|---|---|---|---|
| 29 | H | Cl | Cl | Cl | 2-tetrahydrofuryl | 130 |
| 30 | H | Cl | Cl | Cl | OH | 183 |
| 31 | H | Cl | Cl | Cl | Me2N(CH2)2 | 95 |

EXAMPLE 6

1,3-Bis((4-chloro-3-(3,5-dichloro)phenylpyrazol-1-yl)methyl)-2,3-dihydrobenzimidazole (Compound 32)

One drop of acetic acid is added to a solution of 2.55 g (0.01 mol) of 4-chloro-3-(3,5-dichloro)phenylpyrazole and 2.4 ml (0.03 mol) of aqueous formaldehyde (37%) in 30 ml of ethanol. A solution of 0.55 g (0.005 mol) of 1,2-phenylenediamine in 10 ml of ethanol is run in dropwise and at room temperature. The mixture is stirred for 5 hours at 60° C. The precipitate is recoverd by filtration, washed with heptane and then dried under reduced pressure. 0.87 g (0.00135 mol) of 1,3-bis((4-chloro-3-(3,5-dichloro)-phenylpyrazol-1-yl)methyl)-2,3-dihydrobenzimidazole is obtained, melting at 170° C.

In the same way, 1,3-bis(4-chloro-3-(3,5-dichloro) phenylpyrazol-1-yl)methyl)-2,3-dihydroimidazole (Compound 33) was obtained, of melting point 139° C.

EXAMPLE 7

8-t-Butyl-2-chloromethyl-1,4-dioxaspiro[4.5]decane 97.0 g (0.597 mol) of 4-t-butylcyclohexanone and 134.7 g (1.184 mol) of 3-chloro-1,2-propanediol are dissolved in 1100 ml of toluene in the presence of 11.5 g (0.060 mol) of PTSA. The mixture is brought to reflux for 6 hours while removing the water formed using a Dean-Stark trap. The reaction mixture is brought to room temperature and washed twice with 1500 ml of an aqueous solution containing 5% of NaHCO₃. The organic phase is dried over MgSO₄ and concentrated under vacuum. The residual oil is used directly in the following step (yield: 99%; NMR analysis).

EXAMPLE 8

8-t-Butyl-2-(cyclohexylaminomethyl)-1,4-dioxaspiro[4.5]decane 6.5 g (0.0250 mol) of 8-t-butyl-2-chloromethyl-1,4-dioxaspiro[4.5]decane and 4.6 g (0.0450 mol) of cyclohexylamine are dissolved in 50 of 95% ethanol in the presence of 5.65 g (0.040 mol) of K₂CO₃ and 0.42 g (0.0025 mol) of KI in an autoclave. The mixture is heated to 180° C. for 8 hours with stirring. After returning to room temperature, the reaction medium is poured into 500 ml of water and extracted with 200 ml of CH₂Cl₂. The organic phase is dried over magnesium sulphate and concentrated under vacuum. The brown oil is used directly in the following step (yield: 98%; NMR analysis).

EXAMPLE 9

4-Chloro-3-(2-nitro-3-chlorophenyl)-1-N-cyclohexyl-1,4-dioxaspiro[4.5]decane-8-(t-butyl)-2-methanaminomethyl)pyrazole (compound 37)

a) 0.40 ml of 1,8-diazabicyclo[5.4.0]undecen-7-ene is added, at room temperature, to a solution of 7.0 g (0.027 mol) of 4-chloro-3-(2-nitro-3-chlorophenyl)pyrazole and 2.40 g of paraformaldehyde in 100 ml of THF. The reaction mixture is stirred for 4 hours at room temperature, concentrated under reduced pressure and taken up in a mixture of 150 ml of water and 150 ml of methylene chloride. The organic phase is dried over magnesium sulphate and concentrated under vacuum. 7.40 g of 1-hydroxymethyl-4-chloro-3-(2-nitro-3-chlorophenyl)pyrazole melting at 146° C. are obtained (yield: 95.5%).

b) 1.25 g (0.0040 mol) of 8-t-butyl-2-(cyclohexylaminomethyl)-1,4-dioxaspiro[4.5]decane dissolved in 10 ml of 95% ethanol are added dropwise, at room temperature, to a solution of 1.21 g (0.0038 mol) of 1-hydroxymethyl-4-chloro-3-(2-nitro-3-chlorophenyl) pyrazole in 10 ml of 95% ethanol. The mixture is stirred for 12 hours at room temperature. The reaction medium is poured into a mixture of 70 ml of water and 70 ml of CH₂Cl₂. The organic phase is dried over magnesium sulphate and concentrated under vacuum. 2.25 g of 4-chloro-3-(2-nitro-3-chlorophenyl)-1-(N-cyclohexyl-1,4-dioxaspiro [4.5]decane-8-(t-butyl)-2-methanaminomethyl)pyrazole are obtained (yield: 99; NMR analysis).

The following compounds of formulae XII and XIII, which are collated in the following tables, were obtained by working in an analogous manner;

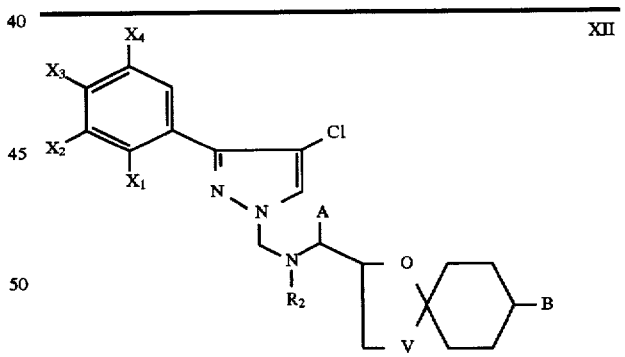

| Compound No. | X1, X2, X3, X4 | R2 | A | V | B | m.p. (°C.) |
|---|---|---|---|---|---|---|
| 38 | NO2, Cl, H, H | n-propyl | H | O | t-Bu | |
| 39 | NO2, Cl, H, H | i-propyl | H | O | t-Bu | |
| 40 | NO2, Cl, H, H | 2-methylaminoethyl | H | O | t-Bu | |
| 41 | NO2, Cl, H, H | 2-methoxyethyl | H | O | t-Bu | |
| 42 | NO2, Cl, H, H | cyclohexylmethyl | H | O | t-Bu | |
| 43 | NO2, Cl, H, H | benzyl | H | O | t-Bu | |
| 44 | NO2, Cl, H, H | furfuryl | H | O | t-Bu | |
| 45 | NO2, Cl, H, H | tetrahydrofurfuryl | H | O | t-Bu | |
| 46 | NO2, Cl, H, H | 2-thienylmethyl | H | O | t-Bu | |
| 47 | NO2, Cl, H, H | 2-morpholin-1'yl ethyl | H | O | t-Bu | |

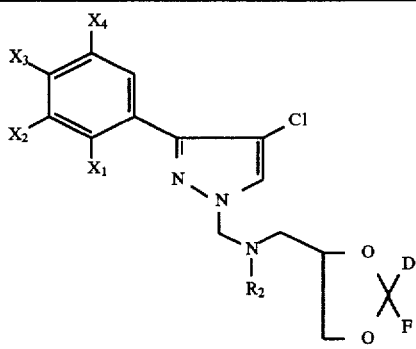

| Compound No. | X1, X2, X3, X4 | R2 | A | F | m.p. (°C.) |
|---|---|---|---|---|---|
| 48 | NO2, Cl, H, H | i-propyl | CH2S(4-Cl—C6H4) | t-Bu | |
| 449 | NO2, Cl, H, H | benzyl | CH2O(4-Cl—C6H4) | t-Bu | |
| 50 | NO2, Cl, H, H | furfuryl | CH3 | i-Bu | |

EXAMPLE 10

In vivo *Botrytis cinerea* test on cucumber

An aqueous suspension, of concentration 1 g/l, of the active material tested is obtained by grinding 60 mg of the latter in the mixture, followed by 5 ml of acetone and 0.3 ml of a surface-active agent (TWEEN 80, oleate of a polyoxyethylenated sorbitan derivative) diluted to a concentration of 10%, and the volume is then adjusted to 60 ml with water.

This aqueous suspension is subsequently diluted with water in order to obtain the desired concentration of active material.

Cucumber plants (Marketer variety) sown on a 50/50 peat soil/pozzolana substrate and grown for 11 days in a greenhouse are treated by spraying with the suspension of active material described above.

Plants used as controls are treated by spraying with an aqueous solution not containing the active material.

24 hours after treatment, the inoculum is supplied by depositing drops of a suspension of *Botrytis cinerea* spores, which are benzimidazole-sensitive or benzimidazole-resistant, obtained from 15-day cultures, subsequently placed in suspension at a rate of 150,000 units per cm3.

After contamination, the plants are placed in a moisture-saturated atmosphere. The merit rating, by comparison with the control plants, is carried out 6 days after contamination.

Under these conditions, a good (at least 75%) or total protection is observed with the Compounds 1 to 11, 14 to 22, 30 and 31 at the dose of 1 g/l.

EXAMPLE 11

In vivo test for *Pyricularia oryzae*, responsible for rice blast disease

By fine grinding, an aqueous suspension of the active material to be tested is prepared having the following composition:

—active material: 60 mg

—Tween 80 surface-active agent (oleate of a polyoxyethylenated sorbitan derivative) diluted to a concentration of 10% in water: 0.3 ml —the suspension is made up to 60 ml with water.

This aqueous suspension is subsequently diluted with water in order to obtain the desired concentration of active material.

Rice, sown in small cups in a 50/50 mixture of enriched peat and pozzolana, is treated at the 10 cm high stage by spraying with the above aqueous suspension.

At the end of 24 hours an aqueous suspension of *Pyricularia oryzae* spores, obtained from a 15-day culture, susbequently placed in suspension at a rate of 100,000 units per cm3, is applied to the leaves.

The rice plants are incubated for 24 hours (25° C., 100% relative humidity), and then placed in observation cells, under the same conditions, for 5 days.

The readings are taken 6 days after contamination.

Under these conditions, a good (at least 75%) or total protection is observed with the following compounds: 1 to 22, 29 and 31, at the rate of 1 g/l.

EXAMPLE 12

In vivo *Alternaria brassicae* test on radish

An aqueous suspension, of concentration 1 g/l, of the active material tested is obtained by grinding 60 mg of the latter in the following mixture:

—acetone: 5 ml

—surface-active agent (TWEEN 80, oleate of a polyoxyethylenated sorbitan derivative) diluted to a concentration of 10%: 0.3 ml and the volume is then adjusted to 60 ml with water.

This aqueous suspension is subsequently diluted with water in order to obtain the desired concentration of active material.

Radish plants (Pernot variety), sown on a 50/50 peat soil/pozzolana suitable and grown in a greenhouse, are treated at the cotyledon stage by spraying with the suspension of active material described above.

Plants used as controls are treated by spraying with an aqueous solution not containing the active material.

24 hours after treatment, the plants are contaminated by spraying with an aqueous solution of spores (40,000 sp/ml) harvested from a 13-day-old culture.

After contamination, the plants are placed in a moisture-saturated atmosphere at 18°–20° C. Merit rating, by comparison with the control plants, is carried out 6 days after contamination.

Under these conditions, a good (at least 75%) or total protection is observed with the Compounds 1, 2, 16, 17, 19, 23 to 28, 30 and 31, at the rate of 1 g/l.

These results clearly show the good fungicidal properties of the derivatives according to the invention against plant fungal diseases due to fungi belonging to the most varied families, such as Phycomycetes, in particular grape downy mildew, Basidiomycetes, in particular rusts *Puccinia sp.*, *Alternaria sp.*, Ascomycetes, Adelomycetes or Fungi Imperfecti in particular *Botrytis sp.* and *Pyricularia oryzae*.

In practical terms, the compounds according to the invention are rarely used alone. These compounds most often form a part of compositions. These compositions, which may be used as fungicidal agents, contain as active material a compound according to the invention as described above, mixed with solid or liquid supports which are acceptable in agriculture and surface-active agents which are also acceptable in agriculture. The usual inert supports and the usual surface-active agents may in particular be used. These compositions also form part of the invention.

These compositions may also contain all sorts of other ingredients such as, for example, protective colloids, adhesives, thickening agents, thixotropic agents, penetrating agents, stabilizers, sequestering agents etc. More generally, the compounds used in the invention may be combined with all of the solid or liquid additives corresponding to the usual formulation techniques.

Generally speaking, the compositions according to the invention usually contain approximately from 0.05 to 95% (by weight) of a compound according to the invention (hereinafter called the active material), one or more solid or liquid supports and, optionally, one or more surface-active agents.

The term "support" in the present account is understood to denote a natural or synthetic organic or inorganic material with which the compound is combined in order to facilitate its application to the plant, to seeds or to the soil. This support is thus generally inert and it must be acceptable in agriculture, in particular on the treated plant. The support may be solid (clays, natural or synthetic silicates, silica, resins, waxes, solid fertilizers etc.) or liquid (water, alcohols, especially butanol, etc.).

The surface-active agent may be an emulsifying, dispersing or wetting agent of the ionic or nonionic type or a mixture of such surface-active agents. There may, for example, be mentioned polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylenated alkyl taurates), phosphoric esters of polyoxyethylenated phenols or alcohols, esters of fatty acids and polyols, and derivatives of the above compounds containing sulphate, sulphonate and phosphate functional groups. The presence of at least one surface-active agent is generally essential when the compound and/or the inert support are not water-soluble and when the application vehicle is water.

Thus, the compositions for agricultural use according to the invention may contain the active materials according to the invention within a very wide range, from 0.05% to 95% (by weight). Their surface-active agent content is advantageously between 5% and 40% by weight.

These compositions according to the invention are themselves in fairly diverse solid or liquid forms.

As solid composition forms, there may be mentioned powders for dusting (at a compound content which may range up to 100%) and granules, in particular those obtained by extrusion, by compacting, by impregnation of a granular support, by granulation from a powder (the compound content in these granules being between 0.5 and 80% for the latter cases), and effervescent lozenges or tablets.

The compounds of formula (I) may also be used in the form of powders for dusting; a composition containing 50 g of active material and 950 g of talc may also be used; a composition containing 20 g of active material, 10 g of finely divided silica and 970 g of talc may also be used; these constituents are mixed and ground and the mixture is applied by dusting.

As liquid composition forms or forms intended to constitute liquid compositions during application, there may be mentioned solutions, in particular water-soluble concentrates, emulsifiable concentrates, emulsions, concentrated suspensions, aerosols, wettable powders (or powders for spraying), pastes and gels.

The emulsifiable or soluble concentrates most often contain 10 to 80% of active material, the emulsions or solutions ready for application themselves containing 0.001 to 20% of active material.

In addition to the solvent, the emulsifiable concentrates may contain, when necessary, 2 to 20% of suitable additives such as the abovementioned stabilizing agents, surface-active agents, penetrating agents, corrosion inhibitors, dyes or adhesives.

Starting from these concentrates and by dilution with water, it is possible to obtain emulsions of any desired concentration, which are particularly suitable for application to the crops.

By way of example, the composition of a few emulsifiable concentrates is given:

EXAMPLE EC 1

| active material | 400 g/l |
|---|---|
| alkali metal dodecylbenzene sulphonate | 24 g/l |
| oxyethylenated nonylphenol containing 10 molecules of ethylene oxide | 16 g/l |
| cyclohexanone | 200 g/l |
| aromatic solvent | q.s. 1 liter |

According to another emulsifiable concentrate formula, the following are used:

EXAMPLE EC 2

| active material | 250 g |
|---|---|
| epoxidized vegetable oil | 25 g |
| mixture of alkylarylsulphonate and ether of polyglycol and fatty alcohols | 100 g |
| dimethylformamide | 50 g |
| xylene | 575 g |

The concentrated suspensions, which may also be applied by spraying, are prepared so as to obtain a stable fluid product which does not form a sediment and they usually contain from 10 to 75% of active material, from 0.5 to 15% of surface-active agents, from 0.1 to 10% of thixotropic agents, from 0 to 10% of suitable additives such as antifoams, corrosion inhibitors, stabilizing agents, penetrating agents and adhesives and, as support, water or an organic liquid in which the active material is insoluble or sparingly soluble: certain solid organic materials or inorganic salts may be dissolved in the support in order to help prevent sedimentation or as antifreeze for the water.

By way of example, a concentrated suspension composition is given:

EXAMPLE CS 1

| active material | 500 g |
|---|---|
| polyethoxylated tristyrylphenol-phosphate | 50 g |
| polyethoxylated alkylphenol | 50 g |
| sodium polycarboxylate | 20 g |
| ethylene glycol | 5.0 g |
| organopolysiloxane oil (antifoam) | 1 g |
| polysaccharide | 1.5 g |
| water | 316.5 g |

The wettable powders (or powder for spraying) are usually prepared so that they contain 20 to 95% of active material, and they usually contain, in addition to the solid support, from 0 to 30% of a wetting agent, from 3 to 20% of a dispersing agent and, when necessary, from 0.1 to 10% of one or more stabilizers and/or other additives, such as penetrating agents, adhesives or anticaking agents, dyes, etc.

In order to obtain the powders for spraying or the wettable powders, the active materials are intimately mixed in suitable mixers with the additional substances and are ground using mills or other suitable grinders. In this way, powders for spraying are obtained for which the wettability and the suspension-forming properties are advantageous; they may be suspended in water in any desired concentration, and these suspensions may be used very advantageously, in particular for application to plant leaves.

Pastes may be produced in place of wettable powders. The conditions and modes of production and use of these pastes are similar to those of the wettable powders or powders for spraying.

By way of example, various wettable powder compositions (or powders for spraying) are given:

EXAMPLE WP 1

| active material | 50% |
|---|---|
| ethoxylated fatty alcohol (wetting agent) | 2.5% |
| ethoxylated phenylethylphenol (dispersing agent) | 5% |
| chalk (inert support) | 42.5% |

EXAMPLE WP 2

| active material | 10% |
|---|---|
| synthetic oxo C13 alcohol of branched type, ethoxylated with 8 to 10 ethylene oxide (wetting agent) | 0.75% |
| neutral calcium lignosulphonate (dispersing agent) | 12% |
| calcium carbonate (inert filler) | q.s. 100% |

EXAMPLE WP 3

This wettable powder contains the same ingredients as in the above example, in the following proportions:

| active material | 75% |
|---|---|
| wetting agent | 1.50% |
| dispersing agent | 8% |
| calcium carbonate (inert filler) | q.s. 100% |

EXAMPLE WP 4

| active material | 90% |
|---|---|
| ethoxylated fatty alcohol (wetting agent) | 4% |
| ethoxylated phenylethylphenol (dispersing agent) | 6% |

EXAMPLE WP 5

| active material | 50% |
|---|---|
| mixture of anionic and nonionic surfactants (wetting agent) | 2.5% |
| sodium lignosulphonate (dispersing agent) | 5% |
| kaolin clay (inert support) | 42.5% |

The aqueous emulsions and dispersions, for example the compositions obtained by diluting with water a wettable powder or an emulsifiable concentrate according to the invention, are included within the general scope of the present invention. The emulsions may be of the water-in-oil or oil-in-water type and they may have a thick consistency like that of a "mayonnaise".

The componds according to the invention may be formulated in the form of water-dispersible granules, which are also included within the scope of the invention.

These dispersible granules, of apparent density which is generally approximately between 0.3 and 0.6, have a particle size which is generally approximately between 150 and 2000 microns, and preferably between 300 and 1500 microns.

The active material content of these granules is generally approximately between 1% and 90%, and preferably between 25% and 90%.

The remainder of the granule is essentially composed of a solid filler and optionally surfactant adjuvants which confer water-dispersibility properties on the granule. These granules may be essentially of two distinct types depending on whether the retained filler is soluble or insoluble in water. When the filler is water-soluble, it may be inorganic or, preferably, organic. Excellent results have been obtained with urea. In the case of an insoluble filler, the latter is preferably inorganic, such as kaolin or bentonite for example. It is then advantageously combined with surface-active agents (in a proportion of 2 to 20% by weight of the granule) more than half of which, for example, consists of at least one dispersing agent, which is essentially anionic, such as an alkali metal or alkaline-earth metal polynaphthalene-sulphonate or an alkali metal or alkaline-earth metal lignosulphonate, the remainder consisting of nonionic or anionic wetting agents such as an alkali metal or alkaline-earth metal alkylnaphthalenesulphonate.

Furthermore, although this is not essential, other adjuvants such as antifoam agents may be added.

The granule according to the invention may be prepared by mixing the necessary ingredients and then by granulation according to several techniques known per se (granulator, fluid bed, atomizer, extrusion etc.). The granulation process generally ends by a crushing, followed by a sieving to the chosen particle size within the abovementioned range.

It is preferably obtained by extrusion, by working as outlined in the examples below.

EXAMPLE DG1

Dispersible granules

90% by weight of active material and 10% of urea pellets are mixed in a mixer. The mixture is then ground in a toothed roll crusher. A powder is obtained which is moistened with approximately 8% by weight of water. The moist powder is extruded in a perforated roll extruder. A granule is obtained which is dried and then crushed and sieved, so as to retain only the granules with a size between 150 and 2000 microns respectively.

EXAMPLE DG2

Dispersible granules

The following constituents are mixed in a mixer:

| | |
|---|---|
| active material | 75% |
| wetting agent (sodium alkyl-naphthalenesulphonate) | 2% |
| dispersing agent (sodium poly-naphthalenesulphonate) | 8% |
| water-insoluble inert filler (kaolin) | 15% |

This mixture is granulated on a fluid bed, in the presence of water, and then dried, crushed and sieved so as to obtain granules with a size between 0.15 and 0.80 mm.

These granules may be used alone, dissolved or dispersed in water so as to obtain the desired dose. They may also be used for preparing combinations with other active materials, in particular fungicides, the latter being in the form of wettable powders or of aqueous suspensions or granules.

As regards the compositions which are suitable for storage and transport, they more advantageously contain from 0.5 to 95% (by weight) of active substance.

Another subject of the invention is the use of the compounds according to the invention for the control of plant fungal diseases by preventive or curative treatment, on the foliage or the propagation material, of the plants or of their place of growth.

We claim:

1. A compound having the formula

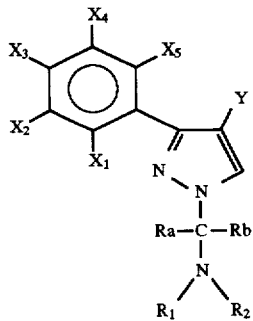

(I)

wherein:

Y is halogen or cyano;

$X_1$, $X_2$, $X_3$, $X_4$ and $X_5$, which are the same or different, are hydrogen, halogen, nitro, $C_1$-$C_4$ alkyl, thiocyanato, amino, $C_2$-$C_5$ alkenyl, $C_2$-$C_5$ alkynyl or $C_1$-$C_4$ alkoxy, with the proviso that at least one of the X substituents is other than hydrogen;

Ra is hydrogen or $C_1$-$C_4$ alkyl;

Rb is hydrogen;

$R_1$ is alkyl, alkoxyalkyl, cyanoalkyl or benzyl, each alkyl and alkoxy having 1 to 4 carbon atoms;

$R_2$ is furfuryl, benzyl, cyanoalkyl, phenyl, alkoxyalkyl or alkyl, each alkyl and alkoxy having 1 to 4 carbon atoms; or $R_1$ and $R_2$, together with the nitrogen atom to which they are attached, form a pyrrolidinyl, piperidinyl, morpholino or thiomorpholino group, said group being optionally substituted by methyl, phenyl or benzyl.

2. A compound as claimed in claim 1, wherein $R_1$ and $R_2$, which are the same or different, are $C_1$-$C_4$ alkyl.

3. A compound as claimed in claim 1, wherein $R_1$ and $R_2$, together with the nitrogen atom to which they are attached, form a pyrrolidinyl, piperidinyl, morpholino or thiomorpholino group, said group being optionally substituted by methyl, phenyl or benzyl.

4. The compound as claimed in claim 1, having the formula

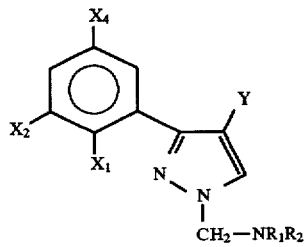

wherein:

(a) Y is Cl, $X_1$ is nitro, $X_2$ is Cl, $X_4$ is H and -$NR_1R_2$ is 2,6-dimethyl-4-morpholinyl;

(b) Y is Cl, $X_1$ is nitro, $X_2$ is Cl, $X_4$ is H and -$NR_1R_2$ is [N-(2-furfuryl)-N-methyl]amino;

(c) Y is Cl, $X_1$ is nitro, $X_2$ is Cl, $X_4$ is H and -$NR_1R_2$ is 1-pyrrolidinyl;

(d) Y is Cl, $X_1$ is nitro, $X_2$ is Cl, $X_4$ is H and -$NR_1R_2$ is 3-methyl-1-piperidyl;

(e) Y is Cl, $X_1$ is nitro, $X_2$ is Cl, $X_4$ is H and -$NR_1R_2$ is 3,5-dimethyl-1-piperidyl;

(f) Y is Cl, $X_1$ is nitro, $X_2$ is Cl, $X_4$ is H and -$NR_1R_2$ is (N-benzyl-N-methyl)amino;

(g) Y is Cl, $X_1$ is nitro, $X_2$ is Cl, $X_4$ is H and -$NR_1R_2$ is 1-piperidyl;

(h) Y is Cl, $X_1$ is nitro, $X_2$ is Cl, $X_4$ is H and -$NR_1R_2$ is N,N-di(cyanoethyl)amino;

(i) Y is Cl, $X_1$ is nitro, $X_2$ is Cl, $X_4$ is H and -$NR_1R_2$ is (N-cyanoethyl-N-methyl)amino;

(j) Y is Cl, $X_1$ is nitro, $X_2$ is Cl, $X_4$ is H and -$NR_1R_2$ is 4-morpholinyl;

(k) Y is Cl, $X_1$ is nitro, $X_2$ is Cl, $X_4$ is H and -$NR_1R_2$ is 4-thiomorpholinyl;

(l) Y is Cl, $X_1$ is nitro, $X_2$ is Cl, $X_4$ is H and -$NR_1R_2$ is diethylamino;

(m) Y is Cl, $X_1$ is nitro, $X_2$ is Cl, $X_4$ is H and -$NR_1R_2$ is 4-phenyl-1-piperidyl;

(n) Y is Cl, $X_1$ is nitro, $X_2$ is Cl, $X_4$ is H and -$NR_1R_2$ is N,N-di(methoxyethyl)amino;

(o) Y is Cl, $X_1$ is nitro, $X_2$ is Cl, $X_4$ is H and -$NR_1R_2$ is 4-methyl-1-piperidyl;

(p) Y is Cl, $X_1$ is H, $X_2$ is Cl, $X_4$ is Cl and -$NR_1R_2$ is [N-cyanoethyl-N-(2-furfuryl)]amino;

(q) Y is Cl, $X_1$ is H, $X_2$ is Cl, $X_4$ is Cl and -$NR_1R_2$ is [N-(2-furfuryl)-N-methyl]amino;

(r) Y is Cl, $X_1$ is H, $X_2$ is Cl, $X_4$ is Cl and -$NR_1R_2$ is 2,6-dimethyl-4-morpholinyl;

(s) Y is Cl, $X_1$ is nitro, $X_2$ is Cl, $X_4$ is H and -$NR_1R_2$ is 4-methyl-1-piperidyl;

(t) Y is Cl, $X_1$ is nitro, $X_2$ is Cl, $X_4$ is H and -$NR_1R_2$ is 4-benzyl-1-piperidyl;

(u) Y is Cl, $X_1$ is nitro, $X_2$ is Cl, $X_4$ is F and -$NR_1R_2$ is 2,6-dimethyl-4-morpholinyl;

(v) Y is Cl, $X_1$ is nitro, $X_2$ is Cl, $X_4$ is F and -$NR_1R_2$ is [N-(2-furfuryl)-N-methyl]amino;

(w) Y is Cl, $X_1$ is F, $X_2$ is Cl, $X_4$ is H and $-NR_1R_2$ is 2,6-dimethyl-4-morpholinyl; or (x) Y is Cl, $X_1$ is F, $X_2$ is Cl, $X_4$ is H and $-NR_1R_2$ is [N-(2-furfuryl)-N-methyl]amino.

5. The compound as claimed in claim 4, wherein Y is Cl, $X_1$ is H, $X_2$ is Cl, $X_4$ is Cl and $-NR_1R_2$ is [N-(2-furfuryl)-N-methyl]amino.

6. A fungicidal composition comprising a fungicidally effective amount of a compound as claimed in claim 1 and an agriculturally acceptable carrier therefor.

7. A fungicidal composition as claimed in claim 6, further comprising an agriculturally acceptable surface-active agent.

8. A fungicidal composition comprising a fungicidally effective amount of a compound as claimed in claim 2 and an agriculturally acceptable carrier therefor.

9. A fungicidal composition comprising a fungicidally effective amount of a compound as claimed in claim 3 and an agriculturally acceptable carrier therefor.

10. A fungicidal composition comprising a fungicidally effective amount of a compound as claimed in claim 4 and an agriculturally acceptable carrier therefor.

11. A fungicidal composition comprising a fungicidally effective amount of the compound as claimed in claim 5 and an agriculturally acceptable carrier therefor.

12. A method for the protection of plants against fungal disease, said method comprising applying to said plants or to the locus in which they grow a fungicidally effective amount of a compound as claimed in claim 1.

13. A method for the protection of plants against fungal disease, said method comprising applying to said plants or to the locus in which they grow a fungicidally effective amount of a compound as claimed in claim 2.

14. A method for the protection of plants against fungal disease, said method comprising applying to said plants or to the locus in which they grow a fungicidally effective amount of a compound as claimed in claim 3.

15. A method for the protection of plants against fungal disease, said method comprising applying to said plants or to the locus in which they grow a fungicidally effective amount of a compound as claimed in claim 4.

16. A method for the protection of plants against fungal disease, said method comprising applying to said plants or to the locus in which they grow a fungicidally effective amount of the compound as claimed in claim 5.

17. A process for the preparation of a compound as claimed in claim 1, said process comprising reacting an aldehyde of the formula RaCH(O) wherein Ra is as defined in claim 14, in the presence of an amine of the formula $R_1R_2NH$ wherein $R_1$ and $R_2$ are as defined in claim 1, with a phenylpyrazole of the formula

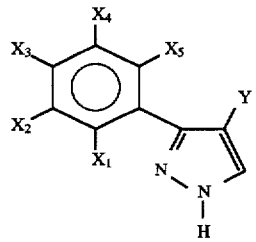

wherein Y, $X_1$, $X_2$, $X_3$, $X_4$ and $X_5$ are as defined in claim 14, at a temperature between room temperature and the reflux point, in a solvent medium, optionally in the presence of a catalytic amount of strong acid.

* * * * *